(12) United States Patent
Koksal et al.

(10) Patent No.: US 10,557,794 B2
(45) Date of Patent: Feb. 11, 2020

(54) OPTICAL SYSTEM FOR MEASURING PRESSURE AND PHASE CHANGES IN FLUIDS

(71) Applicants: Colorado School of Mines, Golden, CO (US); Kaia Corp., Denver, CO (US)

(72) Inventors: Yusuf Akin Koksal, Denver, CO (US); Necati Umit Kaya, Denver, CO (US); Xiaolong Yin, Littleton, CO (US); Erdal Ozkan, Highlands Ranch, CO (US)

(73) Assignees: Colorado School of Mines, Golden, CO (US); Kaia Corp., Denver, CO (US)

( * ) Notice: Subject to any disclaimer, the term of this patent is extended or adjusted under 35 U.S.C. 154(b) by 0 days.

(21) Appl. No.: 15/936,181

(22) Filed: Mar. 26, 2018

(65) Prior Publication Data
US 2018/0275051 A1 Sep. 27, 2018

Related U.S. Application Data

(60) Provisional application No. 62/476,422, filed on Mar. 24, 2017.

(51) Int. Cl.
*G01J 3/00* (2006.01)
*G01N 21/45* (2006.01)
(Continued)

(52) U.S. Cl.
CPC ............. *G01N 21/45* (2013.01); *G01L 11/02* (2013.01); *G01N 21/4133* (2013.01); *G01N 33/2823* (2013.01); *G01N 2201/06113* (2013.01)

(58) Field of Classification Search
CPC ........ G01J 21/34; G01J 21/33; G01J 21/3504; G01J 3/10; G01J 3/42
(Continued)

(56) References Cited

U.S. PATENT DOCUMENTS

| 5,218,197 A | 6/1993 | Carroll |
| 6,130,439 A | 10/2000 | Menn |

(Continued)

OTHER PUBLICATIONS

Birch et al., "An Updated Edlén Equation for the Refractive Index of Air," Metrologia, vol. 30, No. 3, 1993, pp. 155-163 [Abstract Only].

(Continued)

*Primary Examiner* — Md M Rahman
(74) *Attorney, Agent, or Firm* — Sheridan Ross PC

(57) ABSTRACT

A system and method of non-intrusively measuring characteristics of a fluid in a substrate are provided. The fluid is located in a fluid channel in a substrate, and an electromagnetic radiation source emits an electromagnetic beam toward the fluid and the substrate such that a first part of the beam reflects off a first surface of the substrate and a second part of the beam travels through the fluid and reflects off a second surface of the substrate. A sensor detects the resulting interference pattern produced by the two parts of the beam. Changes in fringes of the interference pattern, such as shifting positions or intensities, relates to a change in the refractive index of the fluid. Since a change in refractive index relates to the density and pressure of the fluid, the changes in interference patterns can be used to discern changes in characteristics in the fluid such as pressure.

5 Claims, 6 Drawing Sheets

(51) Int. Cl.
  *G01L 11/02*    (2006.01)
  *G01N 33/28*    (2006.01)
  *G01N 21/41*    (2006.01)

(58) Field of Classification Search
  USPC .......................................................... 356/51
  See application file for complete search history.

(56) References Cited

U.S. PATENT DOCUMENTS 7,130,060 B2   10/2006  Bornhop et al.
8,502,985 B2    8/2013  Weinberger et al.

OTHER PUBLICATIONS

Edlen, "The Refractive Index of Air," Metrologia, vol. 2, No. 2, 1965, pp. 71-80 [Abstract Only].

OPTICAL SYSTEM FOR MEASURING PRESSURE AND PHASE CHANGES IN FLUIDS

CROSS REFERENCE TO RELATED APPLICATIONS

This application claims priority and benefits under 35 U.S.C. § 119(e) to U.S. Provisional Patent Application Ser. No. 62/476,422 filed on Mar. 24, 2017, which is incorporated herein in its entirety by reference.

FIELD OF INVENTION

The present invention generally relates to systems and methods for measuring a characteristic of a fluid using refractive indices and resulting interference patterns.

BACKGROUND

Large amounts of oil and gas are located in unconventional reservoirs such as shale formations. Shale formations are tight-rock formations that have reasonable porosity (3-8%) but low permeability (i.e., less than about 0.1 millidarcy rocks). Unlike traditional oil and gas reservoirs, shale formations produce oil and gas from rock formations with flows which, in some cases, are less permeable than concrete.

By the early 2000s, the oil and gas industry showed it could produce oil and gas economically from shale formations. Bringing shale formations into production required innovations in both drilling (e.g., long horizontal wells) and hydraulic fracturing (e.g., high-pressure, high-volume, isolated, multi-staged injections). Hydraulic fracturing creates networks of micro-fractures which extend great distances from the wellbore. The production flows through these micro crack networks linking the porosity to larger fractures near the wellbore.

Understanding the behavior of pressurized micro-cracks is critical to understanding, managing, and predicting production behavior and lifetime of shale formations. These, in turn, are important to the economic success of any field or reservoir. The characteristics of oil flow through highly flow-restrictive shales is not as well understood and has not been accurately quantified compared to conventional oil reservoirs.

Understanding the role of micro-fractures in the development, production, and management of shale formations requires measurement and quantification of the flow and phase behavior of the hydrocarbons and any other fluids in the micro-fractures and the nearby pores. As production develops, pressure in the reservoir changes and a rich gas may condense into liquid in the nano-pores adjacent to a micro fracture, reducing (or otherwise changing) the rate of mass transfer.

Quantifying pressure and the pressure-dominated changes and including that data in reservoir simulation models would be very useful to managing, maintaining, and optimizing production. Unfortunately, at present, there is no device or sensor known that can make quantitative pressure measurements in the micro-scale flow channels that are experienced in shale formations.

More specifically, conventional pressure measurement systems couple directly into the fluid where the measurement is needed. Stated differently, a sensing element of the measurement system is connected to, or inserted in, the fluid. The pressure of the fluid physically displaces or deflects the sensing element. The measurement system then either converts the deflection or displacement to a pressure reading or sends a signal to a readout or recording device. The key to these conventional systems is the direct coupling between the measurement system and the targeted fluid.

Conventional systems are intrusive and are thus normally applicable for measuring pressure only in large applications which allow the necessary system-fluid coupling. These conventional systems are not applicable for small applications since, by coupling with the fluid, they deform the setup and corrupt the measurements. For example, these conventional systems may alter the pressure of the fluid being measured. In some cases, the sensing element of the conventional system is simply too large to directly couple to fluids in small chambers, such as the nano-pores and a micro fractures within shale production fields. Thus, known pressure measuring systems are not applicable for pressure measurements needed in small cracks or small crack networks.

Because conventional systems cannot make quantitative pressure measurements in micro-scale flow channels, flow and phase characteristics within micro-fractures are currently visualized and measured using specialized porous media micro models. However, pressure as a controlling variable cannot be directly measured by these models. Hence this data must be recorded in laboratory simulations. One drawback of these laboratory simulations is that they are costly, crude, time consuming to employ, and inaccurate.

An example of one simulation system is the Automated Centrifuge System-ACES-300 by Corelabs. The ACES-300 utilizes centrifugal methods to measure capillary pressure inside core samples obtained from a producing formation during drilling. This system does not consider how characteristics of the core sample may change during actual production of the related reservoir. The conventional pressure measurement system employed by the oil and gas industry and the porous media research community measures fluid pressure on the scale of hard-to-recover core samples. Conventional systems, unfortunately, cannot identify pressure within individual pores. Further, conventional systems do not give any information about fluid movement as the reservoir condition changes through production and enhance oil recovery (EOR) operations. Thus, the data from flow tests of cores captured during drilling give very imprecise and inaccurate data about initial reservoir conditions and is not indicative of how production may change during the lifetime of the reservoir.

Further background information can be found in: Birch, Downs, *An updated Edlén Equation for the Refractive Index of Air*, Metrologia 30:155-163, 1993, available at http://iopscience.iop.org/article/10.1088/0026-1394/30/3/004/meta;jsessionid=DAC59C333911E92EA3800B892EBFAD2D.c2.iopscience.cld.iop.org; and Bengt Edlén, *The Refractive Index of Air*, Metrologia, 2:71-80, 1966, available at http://iopscience.iop.org/article/10.1088/0026-1394/2/2/002/meta which are each incorporated herein by reference in their entirety. To provide additional background and context, the following references are incorporated by reference herein in their entireties: U.S. Pat. Nos. 5,218,197; 6,130,439; 7,130,060; and 8,502,985.

Due to the limitations associated with conventional pressure measurement systems and modeling techniques there is an unmet need for a system and method of measuring pressure and phase changes in a fluid that does not require coupling directly to the fluid.

SUMMARY

One aspect of the present invention is to provide systems and methods of measuring characteristics of a fluid non-intrusively and without deforming the fluid. In some embodiments, an electromagnetic radiation source emits an electromagnetic beam at a substrate and a fluid within the substrate. The electromagnetic beam splits with one beam reflecting off a first surface and another beam traveling through the fluid and reflecting off a second surface. As the two beams emerge from the substrate, the two beams interact and create an interference pattern with bright fringes produced by constructive interference and dark fringes produced by destructive interference. A sensor can detect these interference patterns. A change in interference patterns relates to a change in refractive index of the fluid. Since the refractive index of the fluid is linked to the density and, thus, the pressure of the fluid, a change in interference pattern relates to a change in a characteristic of the fluid such as pressure.

One aspect of the present invention is to provide at least one pump to alter the pressure of the fluid within the channel. The at least one pump may be positioned to one or more of push the fluid into the channel and to pull the fluid out of the channel. Pressure changes in the fluid cause the index of refraction of the fluids to change which, in turn, causes the fringe pattern to change and move. Each recorded fringe pattern is calibrated to a pressure. Once a set of interference patterns and fringes changes is established, embodiments of the present invention can be used to determine, for example, an unknown pressure of a fluid.

In some embodiments, the system includes a computing system to analyze the interference pattern recorded by the sensor. The computing system may be in operable communication with the pump, the sensor, and any other components to coordinate the various components. For example, the computing system may send a signal to the pump to change the pressure of the fluid within the substrate and have the sensor timed to record the resulting interference pattern.

In some embodiments, the channel can have four sides and two ends in a generally rectangular shape. At least one of the sides of the channel can have a substantially linear surface. However, surfaces of the sides may also be irregular such as to simulate the surface of rock. In one embodiment, the sides of the channel may be generally parallel. Alternatively, at least one side may diverge from an opposing side. In various embodiments, the channel is a micro-fracture of rock-simulating, transparent micro fluidic micro models. In another embodiment, the channel comprises micro-fractures in slices of real rock. In one embodiment, at least one side of the channel is at least partially transparent to electromagnetic radiation generated by an electromagnetic radiation source.

Yet another aspect is a system that can characterize and quantify fluid movement within flow-restrictive materials, such as shales which are encountered in unconventional oil and gas reservoirs. In one embodiment, the system can remotely measure the flow of fluids in micro-fractures. In another embodiment, the micro-fractures may simulate conditions in a hydrocarbon reservoir. For example, in one embodiment, the micro-fractures have at least one of a size and a cross-section substantially the same as micro-cracks of shale.

It is one aspect of the present invention to provide a system which can characterize and quantify fluid movement within an unconventional reservoir, such as a shale formation. Another aspect of the present invention is a system that can test changing conditions within microcracks (e.g., pressure and size of microcracks) simulating changing conditions in the reservoir. In one embodiment, data obtained using the system can be input directly into reservoir simulation programs. These reservoir simulation programs may subsequently be used by oil and gas producers to predict production from shale formations and control associated costs.

Although generally referred to herein as a "crack" or a "micro-crack," it should be appreciated that the current invention may be used to measure pressure and phase changes of fluids in channels of any size and shape. Accordingly, the terms "crack" and "micro-crack" are intended to cover channels for fluids of any size or shape. Thus, the system and method may be used with substrates including one or more channels and the channels may have a variety of depths, widths, shapes, and lengths. As used herein, a "fluid" is a substance that continually deforms (flows) under an applied shear stress. One of skill in the art will appreciate that fluids are substances that have zero shear modulus, or, in simpler terms, a fluid is a substance which cannot resist any shear force applied to it. Accordingly, the term "fluid" includes matter in one or more of a liquid and a gaseous phase.

One particular embodiment of the present invention is a method of measuring a fluid characteristic. The method can comprise multiple steps including providing a fluid channel that is at least partially defined by a substrate material, which has a refractive index. A fluid having the fluid characteristic to be measured is provided in the fluid channel. The fluid also has a refractive index and is provided in the fluid channel at a first pressure.

Next, an electromagnetic radiation beam is directed to the substrate material and the fluid within the substrate material. It will be appreciated that the steps described herein can be performed by various components and/or features. For instance, the initial electromagnetic radiation beam can be produced by a helium-neon laser. A first beam of the electromagnetic radiation beam reflects off a first surface of the substrate material and travels along a path dictated by the refractive index of the substrate material. A second beam of the electromagnetic radiation beam travels through the fluid and reflects off a second surface of the substrate material, travels back through the fluid, and travels through the substrate material along a path dictated by the refractive indices of the substrate material and the fluid. The first and second beams emerge from the substrate material and interact to produce an interference pattern, which can be detected and compared to other interference patterns to measure a characteristic of the fluid.

It will be appreciated that a subsequent interference pattern can be produced and detected in a same or similar manner where, for example, the pressure of the fluid is changed for the detection of the second interference pattern, and the fluid characteristic is at least one of a phase change of the fluid and a pressure change of the fluid. One way to characterize changes between interference patterns is to detect a first position of a fringe in the first interference pattern relative to a reference point and then detect a second position of the fringe in the second interference pattern relative to the reference point. Comparing the positions of the fringe can determine a fringe shift, which is used to determine the fluid characteristic of the fluid. Changes like the fringe shift can be linked to the refractive index of the fluid, and a relative change in refractive index over 20% can correspond to a phase change in the fluid.

Another particular embodiment of the present invention is a system for measuring a characteristic of a fluid in a subterranean formation. The system comprises an electromagnetic radiation source, a sensor, and a computing system. The electromagnetic radiation source is configured to emit an electromagnetic beam toward a fluid channel having a fluid such that a first beam of the electromagnetic beam reflects off a first surface of the fluid channel and a second beam travels through the fluid and reflects off a second surface of the fluid channel. The sensor detects an interference pattern produced by the first and second beams, and the interference pattern has at least one fringe. In various embodiments, the electromagnetic radiation source is a helium-neon laser.

The computing system has at least one processor and a non-transitory computer readable medium operably connected to the at least one processor, the non-transitory computer readable medium having stored thereon a set of instructions that, when executed by the at least one processor, causes the computing system to perform operations. The operations can include, for example, receiving interference patterns from the sensor, where a first interference pattern has at least one fringe in a first position and a second interference pattern has the at least one fringe in a second position, and then comparing the first and second positions to determine a fringe shift.

The operations can further include comparing the first and second interference patterns to determine a relative change in the refractive index of the fluid over 20%, which indicates an anomaly. In some embodiments, the anomaly can be used to determine a characteristic of the fluid such as a phase change or a pressure change of the fluid. The computer system can also include operations that determine a fringe pitch of the at least one fringe of the interference pattern in the first instance, and that determine a fringe intensity of the at least one fringe of the interference pattern in the first instance.

Yet another particular embodiment of the present invention is an apparatus for measuring a characteristic of a fluid in a subterranean formation. The apparatus comprises a substrate with a fluid channel and a fluid in the fluid channel, and also comprises a pump operably connected to the fluid channel to control a pressure of the fluid. The apparatus further comprises an electromagnetic radiation source and a sensor used to produce and detect interference patterns, respectively. The electromagnetic radiation source is configured to emit an initial electromagnetic beam at the substrate and the fluid in the fluid channel, and the initial electromagnetic beam comprises a first electromagnetic beam and a second electromagnetic beam. The sensor is configured to receive the first electromagnetic beam reflected off a first surface of the substrate and receive the second electromagnetic beam reflected through the fluid in the fluid channel and off a second surface of the substrate.

In a first instance, the pump sets the fluid to a first pressure, the electromagnetic radiation source emits the initial electromagnetic radiation beam, and the sensor detects the resulting interference pattern. Similarly, in a second instance, the pump sets the fluid to a second pressure, the electromagnetic radiation source emits the initial electromagnetic radiation beam, and the sensor detects the resulting interference pattern. The first and second interference patterns have at least one fringe pattern, and a comparison between the interference patterns determines a change in position of the at least one fringe that correlates to the change in pressure of the fluid.

In addition, the apparatus can detect a first intensity and second intensity of the at least one fringe in the first and second interference patterns, respectively. An increase in intensity or amplitude of constructive interference generally indicates an increase in pressure.

It will be appreciated that various components and materials can be used with this apparatus. For instance, the fluid can be a hydrocarbon, and the electromagnetic radiation source and the sensor can be positioned at predetermined angles with respect to the substrate. The substrate can be comprised of an optically transparent material in some embodiments. A vibration dampener can be added to the apparatus where the vibration dampener reduces the amplitude of a vibration from the external environment to the components of the apparatus including the electromagnetic radiation source, the substrate, and/or the sensor. A transfer cell can be included in the apparatus to reduce contamination of the fluid as the pump changes the pressure of the fluid.

Figure 1:
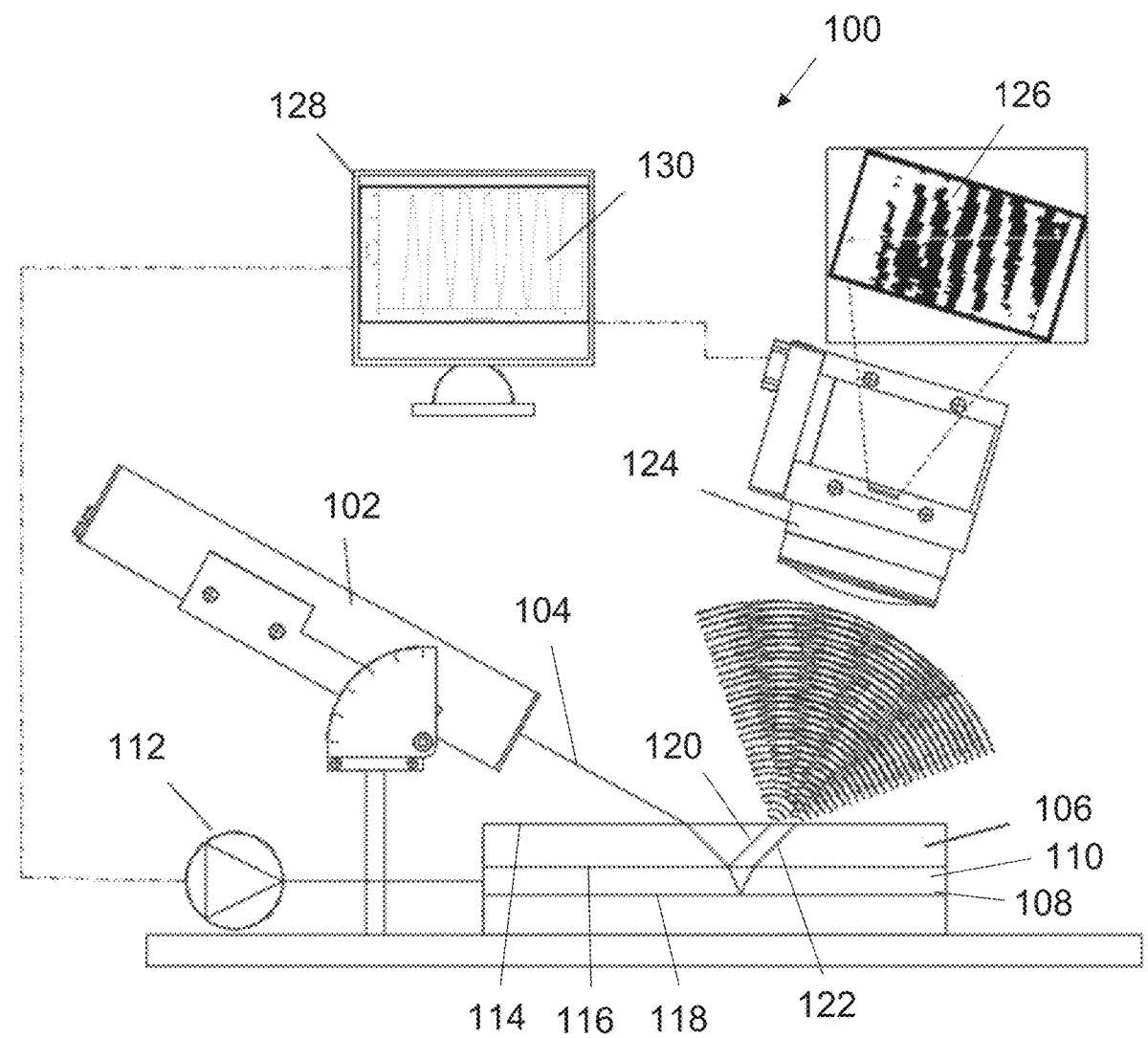
FIG. 1 is a schematic diagram of a system for measuring characteristics of a fluid according to one aspect of the present invention.

A list of the various components shown in the drawings and associated numbering is provided herein:

| Number | Component |
| --- | --- |
| 100 | System |
| 102 | Electromagnetic Radiation Source |
| 104 | Initial Electromagnetic Beam |
| 106 | Substrate |
| 108 | Fluid Channel |
| 110 | Fluid |
| 112 | Pump |
| 114 | Top Surface |
| 116 | First Surface |
| 118 | Second Surface |
| 120 | First Electromagnetic Beam |
| 122 | Second Electromagnetic Beam |
| 124 | Sensor |
| 126 | Received Data |
| 128 | Computing System |
| 130 | Processed Data |
| 132 | Goniometer |
| 134 | Vibration Dampener |
| 136 | Radiation Source Motor |
| 138 | Substrate Motor |
| 140 | Sensor Motor |
| 142 | Additional Sensor |
| 144 | Bright Fringe |
| 146 | Dark Fringe |

-continued

| Number | Component |
|---|---|
| 148 | Tracked Fringe |
| 150 | Fringe Position |
| 152 | Fringe-to-Fringe Pitch |

DETAILED DESCRIPTION

Now referring to FIG. 1, a system 100 for measuring a characteristic of a fluid 110 is provided. Generally, the system 100 relies on an electromagnetic radiation source 102, a refractive index of the fluid 110, and a refractive index of a substrate 106 in which the fluid 110 is positioned to produce an interference pattern that changes with the characteristic of the fluid 110. For instance, a changing interference pattern can represent a changing refractive index of the fluid 110, which is a function of the density and the pressure of the fluid 110. Therefore, detecting a change in interference pattern can represent a change of pressure of the fluid 110. In the depicted embodiment, the substrate 106 defines a fluid channel 108 that contains a fluid 110, which can be a gas or a liquid, for example, a hydrocarbon.

A pump 112 is operably connected to the fluid channel 108 to set the fluid 110 to a known pressure, which changes the refractive index of the fluid 110. The pump 112 can be an incremental, micro-volumetric pump/compressor that is coordinated with a sensor and a computing system, as described in further detail below. The pump 112 can control the pressure of the fluid 110 in increments in the range of millibars and per milliliter, and the pump 112 can hold the pressure of the fluid 110 constant or vary the pressure over time. It will be appreciated that in wellbore operations, the external environment, drilling operations, or resource extraction operations can result in a pressure change that is detectable by embodiments of the present invention.

In operation, the electromagnetic radiation source 102 emits an initial electromagnetic beam 104 at an impingement angle toward the fluid 110 and the substrate 106. The electromagnetic radiation source 102 may be one or more of a light source with a specific wavelength and a combination of light sources with a known spectrum of wavelengths. For example, the electromagnetic radiation source 102 can be a helium-neon laser that produces a monochromatic, collimated light beam. In some embodiments, the helium-neon laser is stabilized and polarized to reduce sources of error in detecting an interference pattern. Further, smaller beam diameter (e.g., ~1 mm) and smaller wavelength can improve the accuracy of a detected interference pattern. The system 100 may further include a mirror (not illustrated) to adjust the path of the initial electromagnetic beam 104.

The electromagnetic radiation beam 104 first contacts a top surface 114 of the substrate 106 and travels through the substrate 106 at an angle dictated by the refractive index of the substrate material, which can be made from an optically transparent material in some embodiments. Then, the beam 104 contacts a first surface 116 of the substrate 106 that, in this embodiment, represents the top surface of the fluid channel 108. This causes the beam 104 to split into a first electromagnetic beam 120 and a second electromagnetic beam 122. The first electromagnetic beam 120 reflects off the first surface 116 upward through the substrate 106. The second electromagnetic beam 122 travels through the fluid 110 according to a refractive index of the fluid, reflects off a second surface 118 of the substrate 106, which is the bottom surface of the fluid channel 108 in this embodiment, and then travels upward through the fluid 110 and the substrate 106.

The beams 120, 122 emerge from the substrate 106 having traveled different paths and through different materials with different refractive indices. The beams 120, 122 interact with each other and, due to the wave-like behavior of electromagnetic radiation, the interacting beams 120, 122 produce an interference pattern with bright fringes (constructive interference) and dark fringes (destructive interference). Changes in fringes between different interference patterns can indicate different characteristics of the fluid 110 including pressure changes, phase changes, etc. For example, a change in fringe position can indicate an increase or decrease in pressure of the fluid 110. In addition, an anomaly in the interference pattern can indicate a phase change in the fluid 110 such as condensation or evaporation.

As shown in FIG. 1, a sensor 124 detects an interference pattern 126, and a computing system 128 can record and manipulate the recorded interference pattern data into processed data 130 for analysis, i.e., detecting anomalies, fringe movements, fringe brightness, fringe pitch, fringe density, fringe order, etc. The computing system 128 is operably connected to the sensor 124 and operably connected to the pump 112 and can control operations of the sensor 124, the pump 112, and any other components described herein. The computing system 128 can direct the pump 112 to hold constant or vary the pressure of the fluid 110 and can coordinate the pump 112 with, for example, a shutter of the sensor 124. As a result, the sensor 124 captures the interference pattern 126 when the fluid 110 is at a known pressure or rate of pressure change. It will be appreciated that while a pressure change and a phase change are referenced herein, an interference pattern can reflect changes in other aspects or characteristics of the fluid. For example, a heating and/or cooling system can impose a thermal gradient, a heat flux, or a simple change in temperature to the fluid that changes the refractive index of the fluid, and thus, results in a different interference pattern. In general, any aspect or characteristic that can change the refractive index of the fluid can be detected by embodiments of the present invention.

In some instances, a strong reflection of the beam 104 produced off the top surface 114 saturates the interference pattern detected by the sensor 124. To minimize this saturation effect, a reflective coating can be applied to the second surface 118 to increase the amount of radiation reflected off of the second surface 118. In addition or alternatively, a wedge shaped portion of the substrate or other material can be added to the top surface 114 to direct the reflected portion of the beam 104 away from the sensor 124. Further still, the material of the substrate itself can be chosen to minimize this saturation effect.

In further instances, ambient electromagnetic radiation from any ambient source can interact with the sensor 124 and cause a type of background noise for the recorded data. To reduce this background noise, a filter can be positioned over the sensor where the filter prevents electromagnetic radiation outside of a predetermined band from entering the sensor 124. In addition, a sensor 124 that is most sensitive or only sensitive to the desired band of electromagnetic radiation can reduce background noise.

Embodiments described herein can record interference patterns based on known pressures provided by the pump 112. These interference patterns can be analyzed for anomalies, fringe movements, fringe brightness, fringe pitch, fringe order, fringe density, etc. With an established set of interference patterns, embodiments described herein can then be used to determine an unknown pressure of a fluid. In addition, embodiments of the present invention can be calibrated for different substrate materials, fluids, refractive indices, etc. The results of this in-situ calibration method can also correct iterated data with recursive calculations. In addition, embodiments of the present invention can be incorporated onto a sub assembly in a drill string or string of pipe to measure unknown pressures in micro cracks within a wellbore or formation.

Methods described herein may comprise one or more steps or procedures, any or all of which can be executed by the computing system 128. As such, an embodiment may provide a computing system 128 configured with instructions to perform one or more steps or procedures in accordance with methods provided by various other embodiments. In some embodiments, instructions are encoded on physical, tangible, and/or non-transitory computer readable media including, but not limited to, optical media, magnetic media, and/or the like.

Figure 2:
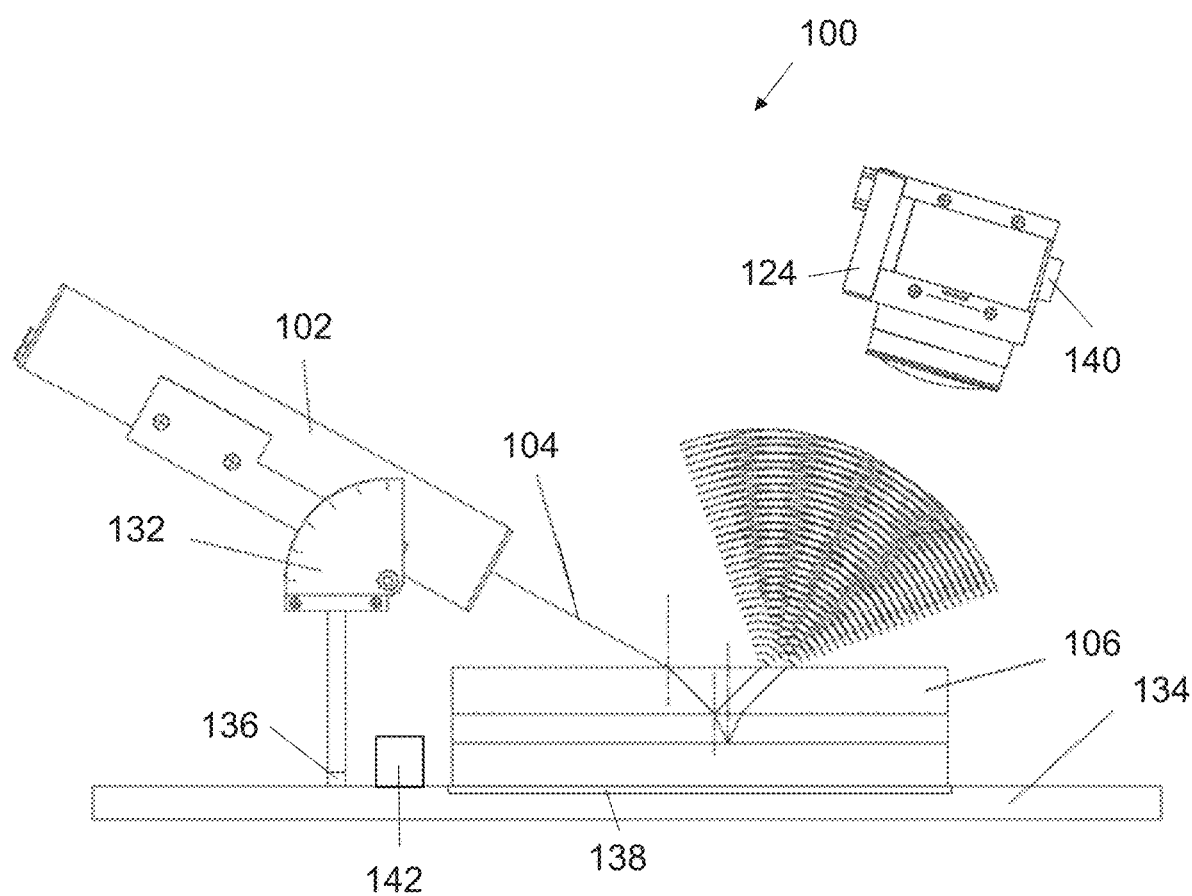
FIG. 2 is a schematic diagram of a further system for measuring characteristics of a fluid according to one aspect of the present invention.

Now referring to FIG. 2, a further depiction of the system 100 is provided. Since the system 100 can be disrupted by the external environment, a vibration dampener 134 can be included. The electromagnetic radiation source 102 and the substrate 106 can be positioned on the vibration dampener 134 to reduce or eliminate vibrations from a ground source or external environment. The system 100 can also optionally include further motors, actuators, goniometers, etc. that move and orient features and components of the system 100. For instance, a goniometer 132 precisely orients the electromagnetic radiation source 102 at an impingement angle relative to the substrate 106. A radiation source motor 136 can move the electromagnetic radiation source 102, a substrate motor 138 can move the substrate 106, a sensor motor 140 can move the sensor 124, etc. Movements can include three dimensional spatial movements, angular movements, and/or rotational movements. Further sensors 142 can detect temperature, relative humidity, $CO_2$, pressure, etc. It will be appreciated that motors and movements can be applied to any features or component described herein including mirrors associated with the electromagnetic radiation source 102, a platform or stage on which components are placed, etc. In addition, the computing system can coordinate these various motors and goniometers to space and orient the various components. Further still, predetermined orientations and spacings between components can be stored by the computing system, which can subsequently and automatically position the components to the predetermined orientations and spacings.

Figure 3A:
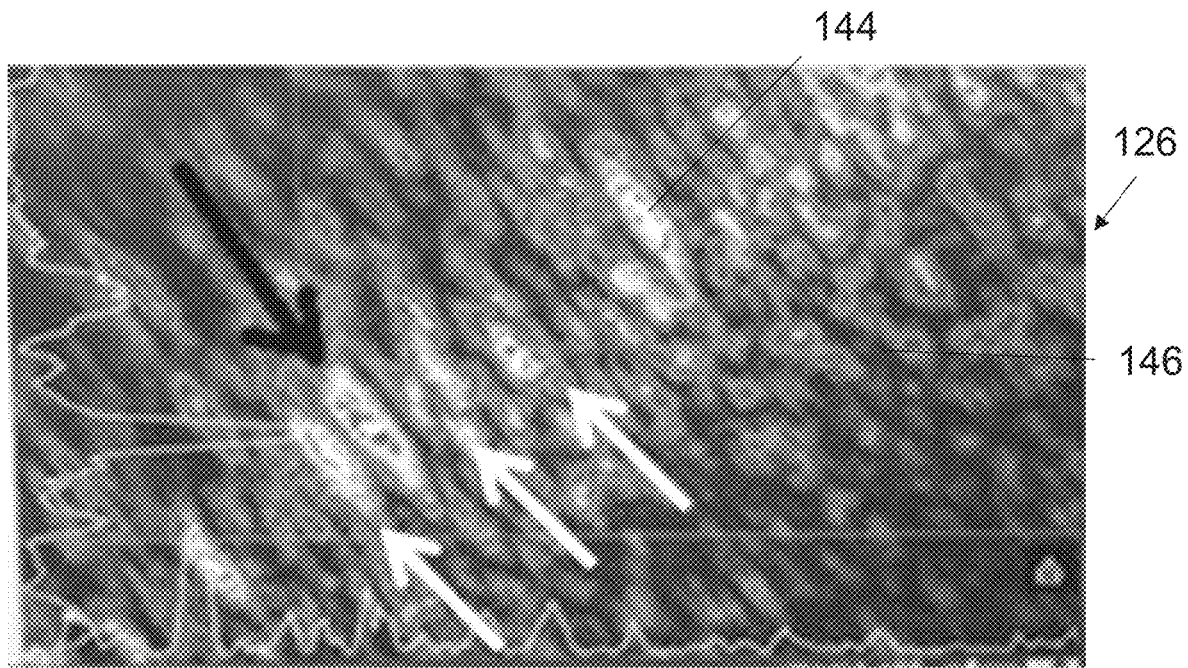
FIG. 3A is an interference pattern at a first pressure according to one aspect of the present invention.
Figure 3B:
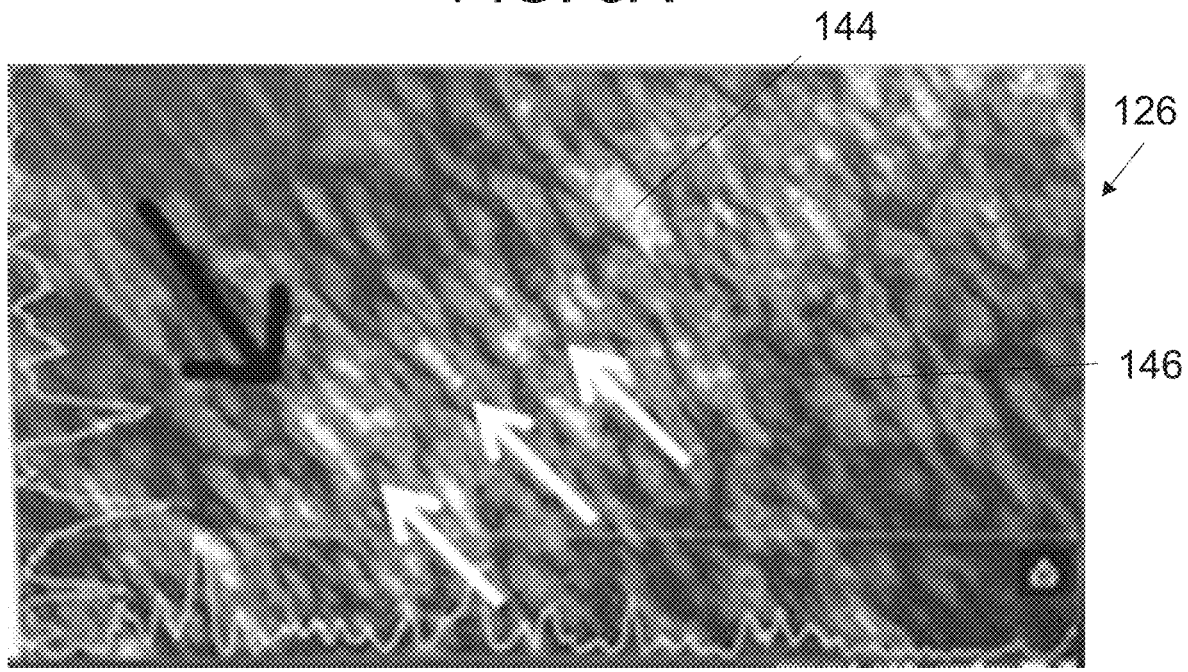
FIG. 3B is an interference pattern recorded after the interference pattern in FIG. 3A at a second pressure according to one aspect of the present invention.

Now referring to FIGS. 3A-3B, an interference pattern 126 at two different pressures is provided. In FIG. 3A, an interference pattern 126 is depicted when the fluid in the fluid channel is at a lower pressure. The interference pattern 126 has bright fringes 144, or areas where two beams produce constructive interference, and the interference pattern 126 has dark fringes 146, or areas where two beams produce destructive interference. In FIG. 3B, the interference pattern 126 is recorded when the fluid is at a higher, second pressure. As a result of the pressure change, the fringes 144, 146 are in different positions, have different intensities or amplitude of detected constructive interference, etc. Generally, the bright fringes are brighter where the fluid is at a high pressure. Analyzing the differences between the interference patterns 126 in FIGS. 3A and 3B can indicate a difference in the refractive index for the fluid, which indicates a change in pressure of the fluid.

Figure 4A:
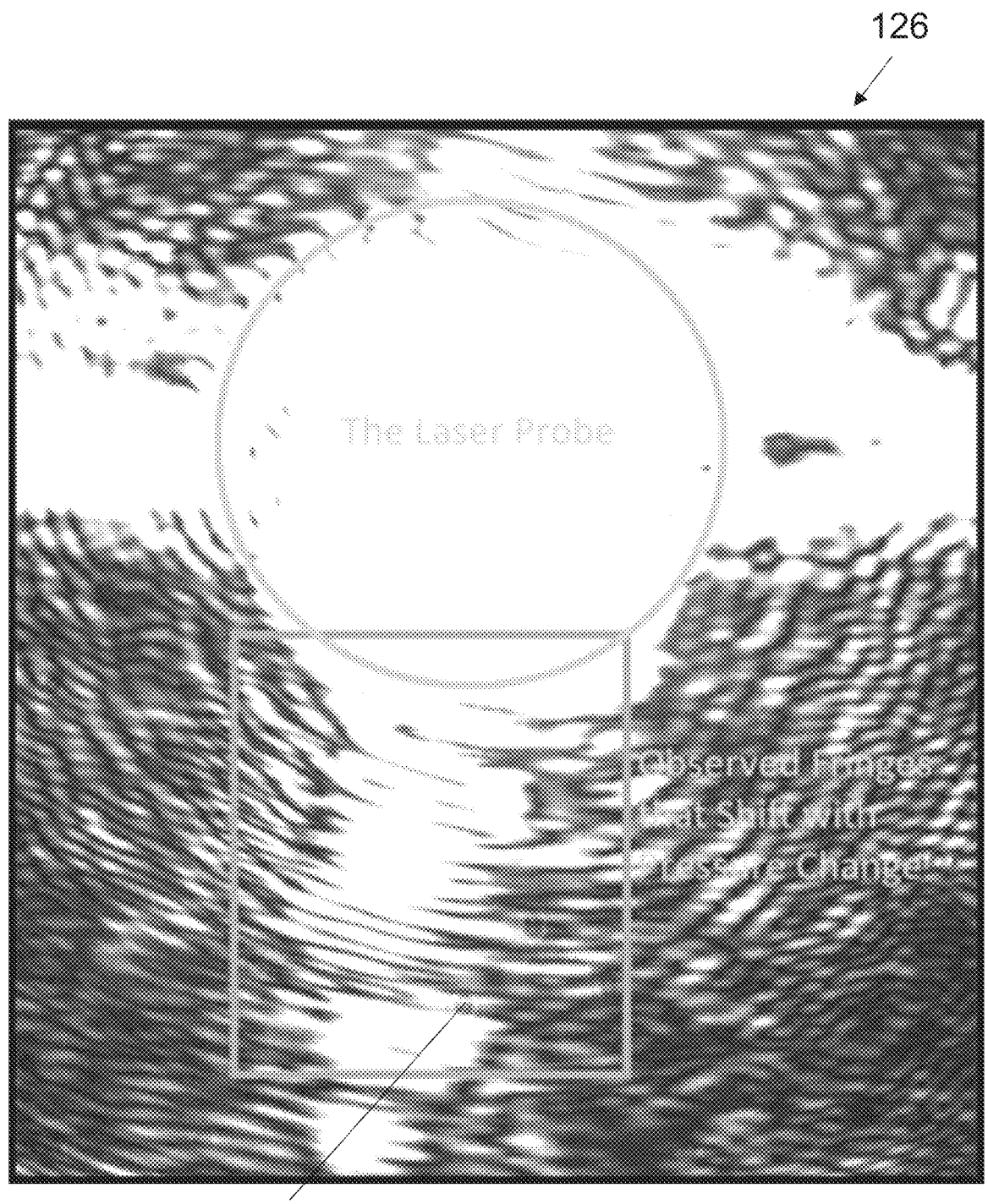
FIG. 4A is another interference pattern at a first pressure according to one aspect of the present invention.
Figure 4B:
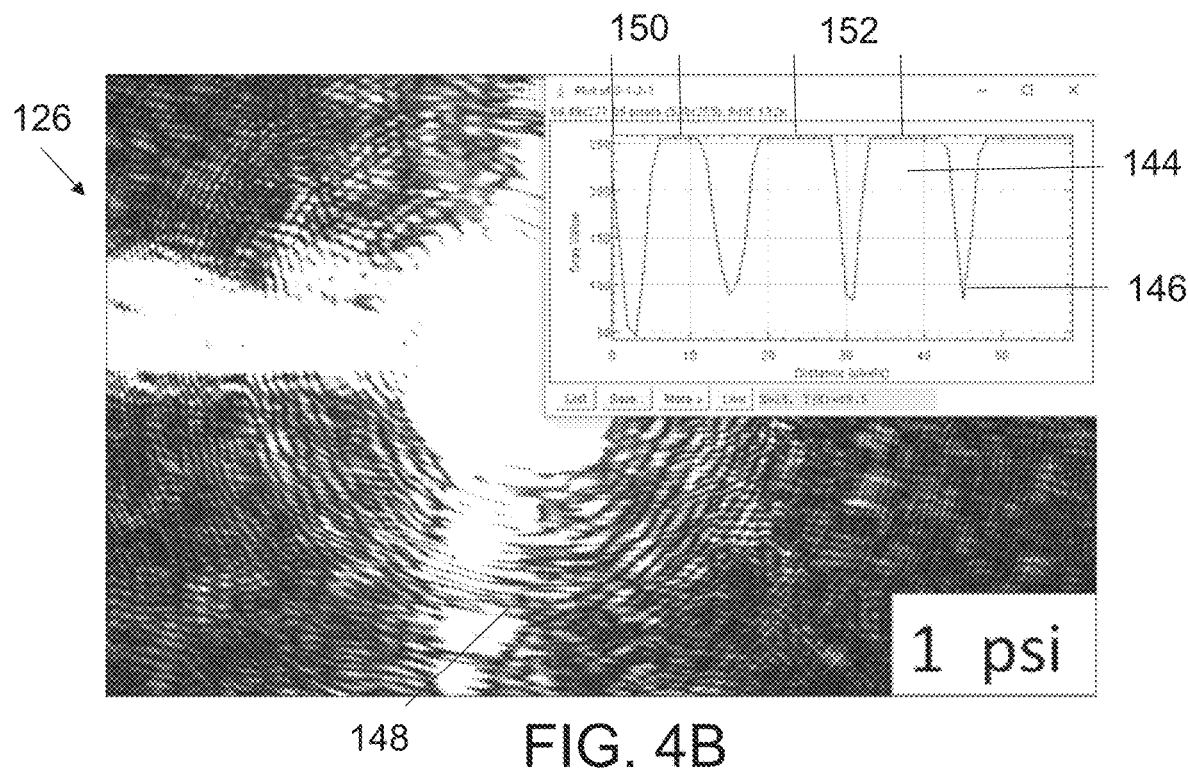
FIG. 4B is another depiction of the interference pattern of FIG. 4A according to one aspect of the present invention.
Figure 4C:
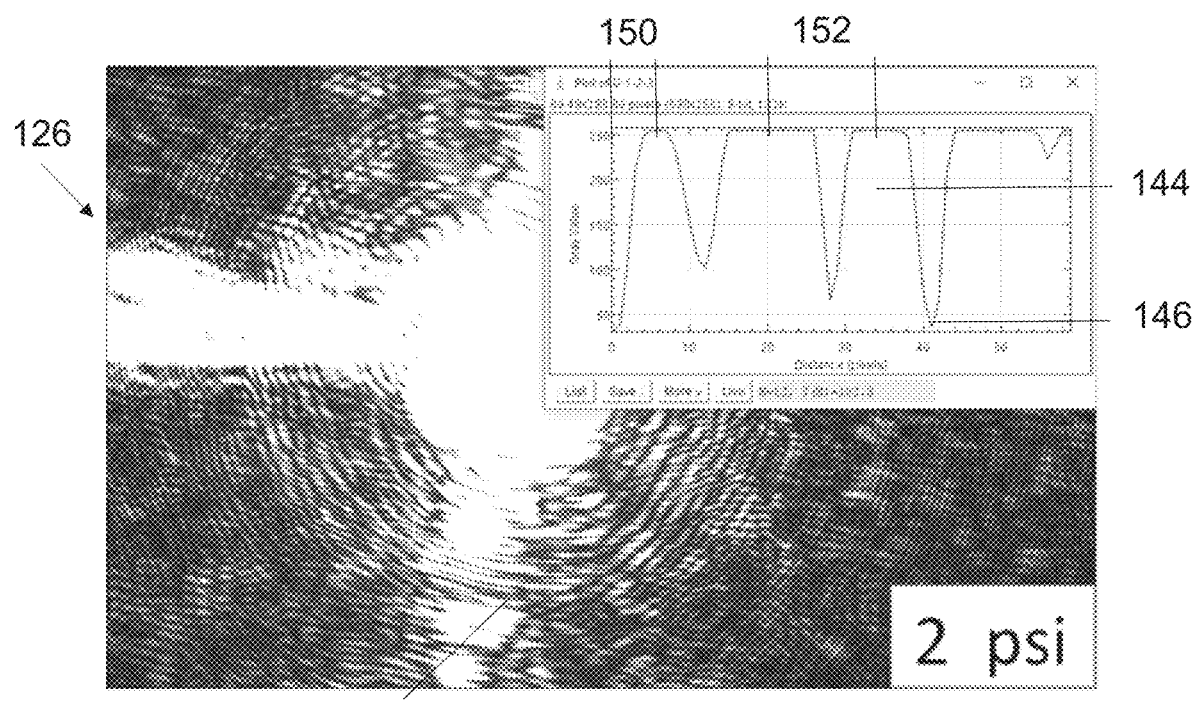
FIG. 4C is an interference pattern recorded after the interference pattern in FIG. 4A at a second pressure according to one aspect of the present invention.

Now referring to FIGS. 4A-4C, another series of interference patterns 126 that show differences in bright fringes 144 and dark fringes 146 is provided. FIG. 4B shows another view of the interference pattern 126 in FIG. 4A, and the interference pattern 126 is produced by a fluid at a pressure of 1 psi. An inset in FIG. 4B shows additional information about the fringes, including a tracked fringe 148. For instance, the inset shows the intensity of bright fringes 144 (peaks) and dark fringes 146 (troughs) versus the position of the fringes 144, 146. Further, a fringe position 150 relative to a reference position such as a center of the interference pattern 126 is depicted as well as a fringe-to-fringe pitch 152. FIG. 4C shows a similar interference pattern 126 and inset as FIG. 4B, but the pressure of the fluid has increased to 2 psi. As a result, the fringes 144, 146 have shifted position 150 along the x axis and have shifted intensity along the y axis. In addition, the fringe-to-fringe pitch 152 has changed. The fringes can also change shape and order. These changes can be used to then interpret an interference pattern for a fluid with an unknown pressure to then determine the pressure of the fluid.

Figure 5A:
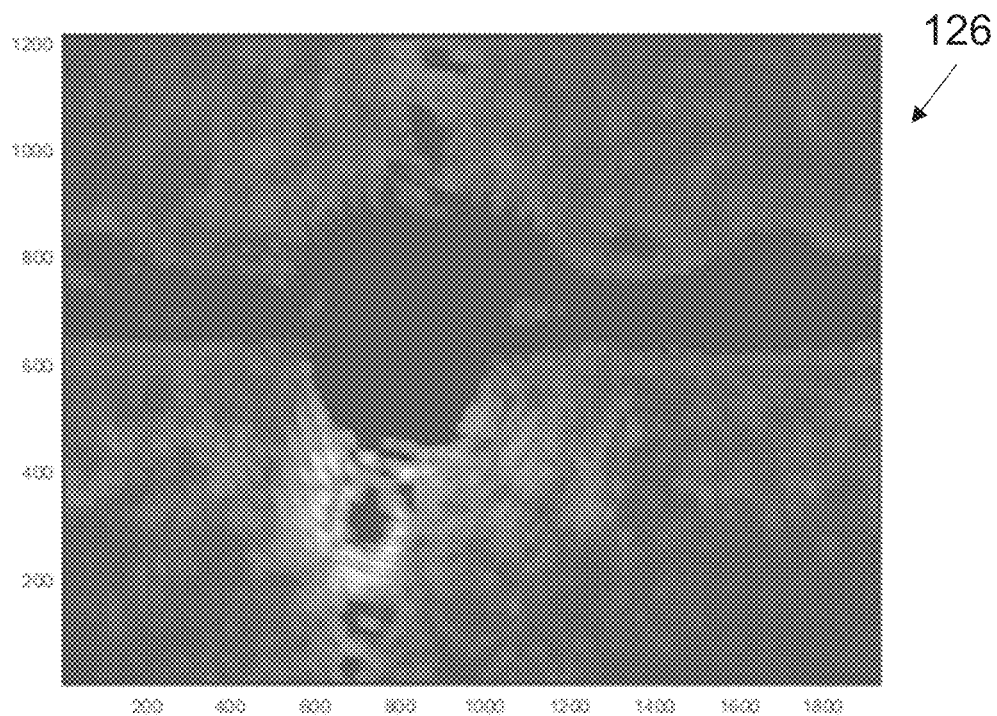
FIG. 5A is another depiction of the interference pattern of FIG. 4A according to one aspect of the present invention.
Figure 5B:
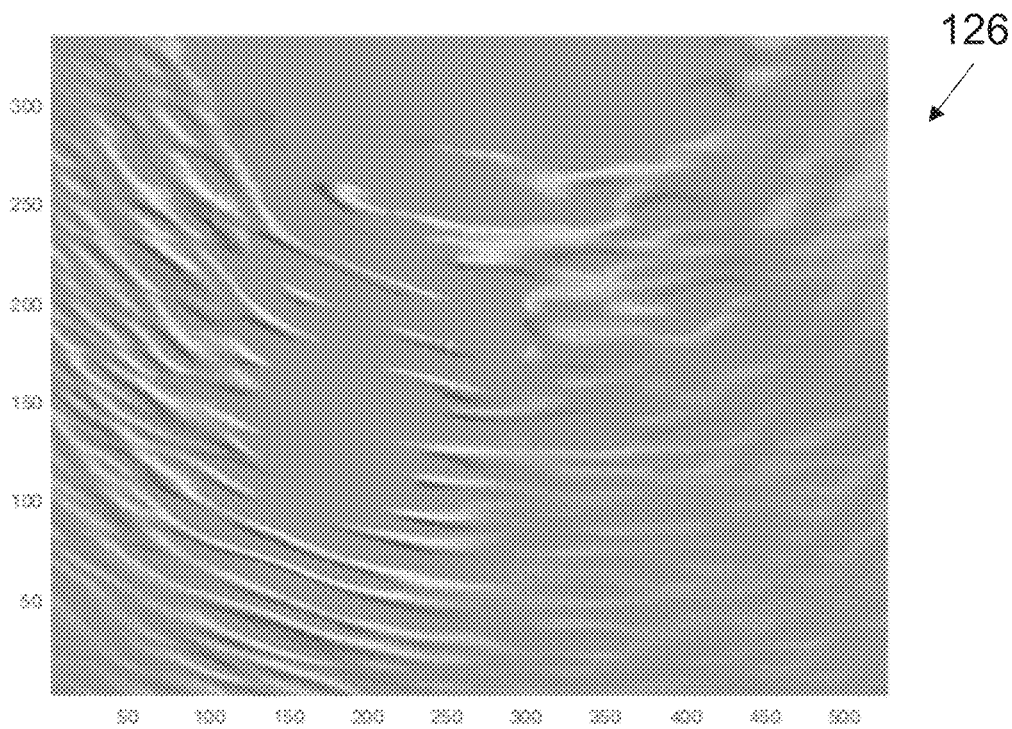
FIG. 5B is yet another depiction of the interference pattern of FIG. 4A according to one aspect of the present invention.

Now referring to FIGS. 5A and 5B, further depictions of the interference pattern 126 of FIG. 4A are provided. FIG. 5A depicts bright and dark fringes using bright and dark colors, respectively. FIG. 5B depicts bright and dark fringes using a different color scale. It will be appreciated that various depictions of an interference pattern can contribute to different analyses of the interference pattern to determine changes such as anomalies, fringe movements, fringe brightness, fringe pitch, fringe order, fringe density, etc.

In one embodiment, an anomaly is characterized by a substantial change in refractive index. For example, gaseous propane at 20° C. and 121.33 psai can condense to a liquid and thus change densities from 18 kg/m$^3$ to 500 km/m$^3$. As a result, the refractive index changes from 1.006 to 1.34, and the interference pattern can have hundreds of different fringes shifting position, which is a number of shifting fringes that is one or more orders of magnitude greater than the number of shifting fringes when a pressure change does not result in a phase change. Accordingly, a relative change in refractive index that is greater than 10% in some embodiments can represent an anomaly and phase change. In further embodiments, a relative change in refractive index that is greater than 20% can represent an anomaly and phase change. In preferred embodiments, a relative change in refractive index that is greater than 30% can represent an anomaly and phase change. When the fluid is comprised of multiple hydrocarbons or other substances, the detection of a phase change can be used to calculate the bubble point pressure and/or the dew point pressure of the fluid.

As noted above, the changes in refractive index determined by the changes in interference pattern can be linked to changes in pressure. Below are a series of equations that can be used to calculate a change in pressure using a change in refractive index. Further below are units and constants used in the equations 1-7. Starting with the polarizability (1), molar polarization (2), the Debye Equation (3), and the relative permittivity (4), the Clausius-Mossotti Equation can be derived as presented below in equation (5). Including the ideal gas law questions of equation (6) to the Clausius-Mossotti Equation, a relationship between pressure and refractive index can be derived as shown below in equation (7). Based on this relationship, detected changes in refractive index can then be used to calculate a change in pressure.

$$\alpha' = \frac{\alpha}{4\pi\varepsilon_0} \tag{1}$$

-continued $$P_m = \frac{N_A \alpha}{3\varepsilon_0} \quad (2)$$

$$\frac{\varepsilon_r - 1}{\varepsilon_r + 2} = \frac{\rho}{M} P_m \text{ (Debye Equation)} \quad (3)$$

$$n^2 = \varepsilon_r \quad (4)$$

$$\frac{n^2 - 1}{n^2 + 2} = \frac{\rho}{M} \frac{4\alpha' \pi N_A}{3} \text{ (Clausius – Mossotti Equation)} \quad (5)$$

$$PV = zRT \frac{m}{M} \text{ and } \frac{m}{V} = \rho = \frac{PM}{zRT} \quad (6)$$

$$P = \frac{n^2 - 1}{n^2 + 2} \frac{3}{4} \frac{zRT}{\alpha' \pi N_A} \quad (7)$$

$\alpha'$ : Polarizability volume, $m^3$ $\alpha$ : Polarizability, $\frac{c^2 \cdot m^2}{J}$ $\varepsilon_0$ : Vacuum Permittivity, $8.854187 \times 10^{12} \frac{c^2}{J \cdot m}$ $P_m$ : Molar Polarization, $\frac{m^3}{\text{mole}}$ $\varepsilon_r$ : Relative permittivity, unitless $\rho$ : Density, $\frac{\text{kg}}{m^3}$ $M$ : Molecular weight, $\frac{\text{kg}}{\text{mole}}$ $n$ : Refractive Index $N_A$ : Avogadro Constant, $6.022141 \times 10^{23} \frac{1}{\text{mole}}$ $P$ : Pressure, $Pa$ $R$ : Universal Gas Constant, $8.314 \frac{Pa \cdot m^3}{K \cdot \text{mole}}$ $T$ : Temperature, K $z$ : Gas compressibility factor, unitless The foregoing description of the present invention has been presented for purposes of illustration and description. Furthermore, the description is not intended to limit the invention to the form disclosed herein. Consequently, variations and modifications commensurate with the above teachings, and the skill or knowledge of the relevant art, are within the scope of the present invention. The embodiment described hereinabove is further intended to explain the best mode known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

The invention claimed is:

1. A method of measuring a fluid characteristic, comprising:
   providing a fluid channel at least partially defined by a substrate material having a refractive index;
   providing a fluid in the fluid channel at a first pressure, the fluid having a refractive index that is different than the refractive index of the substrate material;
   transmitting an initial electromagnetic radiation beam to the substrate material and the fluid, wherein the initial electromagnetic radiation beam comprises a first electromagnetic radiation beam and a second electromagnetic radiation beam;
   reflecting the first electromagnetic radiation beam off a first surface of the substrate material, and reflecting the second electromagnetic radiation beam through the fluid and off a second surface of the substrate material;
   detecting a first interference pattern produced by the reflected first and second electromagnetic radiation beams; and
   comparing the first interference pattern to a second interference pattern to determine a fluid characteristic;
   providing the fluid in the fluid channel at a second pressure;
   transmitting a further initial electromagnetic radiation beam to the fluid channel and the fluid, wherein the further initial electromagnetic radiation beam comprises a third electromagnetic radiation beam and a fourth electromagnetic radiation beam;
   reflecting the third electromagnetic radiation beam off the first surface of the substrate material, and reflecting the fourth electromagnetic radiation beam through the fluid and off the second surface of the substrate material; and
   detecting the second interference pattern produced by the reflected third and fourth electromagnetic radiation beams.

2. The method of claim 1, wherein the fluid characteristic is one of a pressure change of the fluid and a phase change of the fluid.

3. The method of claim 1, further comprising:
   detecting a fringe in the first interference pattern, the fringe having a first position relative to a referent point of the first interference pattern;
   detecting the fringe in the second interference pattern, the fringe having a second position relative to the referent point of the second interference pattern; and
   comparing the first position of the fringe to the second position of the fringe to determine a fringe shift, which is used to determine the fluid characteristic of the fluid.

4. The method of claim 1, wherein the initial electromagnetic radiation beam is produced by a helium-neon laser.

5. The method of claim 1, further comprising:
   detecting an anomaly when comparing the first interference pattern and the second interference pattern by detecting a relative change in refractive index over 20%, wherein the anomaly corresponds to a phase change of the fluid.

* * * * *